(12) United States Patent
Mische

(10) Patent No.: US 7,300,449 B2
(45) Date of Patent: Nov. 27, 2007

(54) METHODS AND DEVICES FOR THE TREATMENT OF NEUROLOGICAL AND PHYSIOLOGICAL DISORDERS

(76) Inventor: Hans A. Mische, 32 Highbanks Pl., St. Cloud, MN (US) 56301

( * ) Notice: Subject to any disclaimer, the term of this patent is extended or adjusted under 35 U.S.C. 154(b) by 648 days.

(21) Appl. No.: 10/843,828

(22) Filed: May 11, 2004

(65) Prior Publication Data

US 2005/0015129 A1 Jan. 20, 2005

Related U.S. Application Data

(63) Continuation-in-part of application No. 10/056,323, filed on Jan. 24, 2002, now Pat. No. 6,764,498, and a continuation-in-part of application No. 09/457,971, filed on Dec. 9, 1999, now Pat. No. 6,375,666.

(51) Int. Cl.
*A61M 29/00* (2006.01)
(52) U.S. Cl. .................................................. 606/198
(58) Field of Classification Search ........ 606/191–198, 606/108; 623/1.15, 1.16, 1.22; 600/411, 600/420, 417, 424, 423; 607/45, 2, 3
See application file for complete search history.

(56) References Cited

U.S. PATENT DOCUMENTS

| | | | | |
|---|---|---|---|---|
| 6,463,317 B1 * | 10/2002 | Kucharczyk et al. | ....... | 600/411 |
| 6,708,064 B2 * | 3/2004 | Rezai | ........................ | 607/45 |

* cited by examiner

*Primary Examiner*—Kevin T. Truong

(57) ABSTRACT

Novel devices and methods that affect the neurologic and biological electrical conduction systems for the treatment various neurological and physiological disorders. Localized mechanical forces imparted by the inventive devices and methods modify or alter the mechanoelectric and or electrochemical properties of the affected tissues and biologic systems. Combinations of various technologies can be incorporated into the devices and methodologies for specific treatments. The devices and methods can be used to treat a number of neurologic and physiologic disorders such as Parkinson's, epilepsy, atrial fibrillation, cardiac arrhythmia, obesity, and others.

18 Claims, 6 Drawing Sheets

METHODS AND DEVICES FOR THE TREATMENT OF NEUROLOGICAL AND PHYSIOLOGICAL DISORDERS

CROSS REFERENCE TO RELATED APPLICATION

This application is a continuation-in-part of application Ser. No. 09/457,971 filed Dec. 9, 1999, now U.S. Pat. No. 6,375,666 and application Ser. No. 10/056,323 filed Jan. 24, 2002 now U.S. Pat. No. 6,764,498.

FIELD OF INVENTION

The present invention relates generally to the treatment of electrical conduction defects in the body. The device and methods are disclosed in the context of treating neurological and physiological disorders that affect a variety of anatomical organs and tissues.

BACKGROUND OF THE INVENTION

The current methods of treating a range of neurological and physiological disorders include the use of systemic drugs, surgical procedures, tissue ablation, electrical stimulation and gene treatments. Many of these disorders are manifested by gross conduction defects. These neurological disorders are may affect many types of anatomical organs and tissues such as brain, heart, muscle, nerves and organ tissues.

SUMMARY

In contrast to the prior art, the present invention proposes treatment of neurological disorders by subjecting selected tissues to localized mechanical stress. It is difficult to quantify the level of stress applied to the tissue; operable values will vary from low levels to high levels dependent on the type and location of tissue to be treated. The tissues treated can be of many types within the body such as the brain, heart, muscles, nerves or organs.

The invention is disclosed in the context of neurological disorders but other the inventive technology can also be used to treat a wide variety of organs and anatomical tissues, and the treatments of other types of ailments are contemplated as well. For example, other applications of this invention include placement in the pituitary, thyroid, and adrenal glands or in a variety of organs. In addition, placement of the inventive device in tumors may suppress growth due to nerve and vascular compression. The later may prevent blood-born metastasis to other parts of the body. Likewise, hemorrhaging can be stopped or reduced by vascular compression using the invention. Pain management in all parts of the body can be achieved by placement of the inventive device adjacent to selected nerves. Positioning an inventive stress-inducing device within the bone can accelerate healing of broken bones. Disclosure of this invention for neurological and neuromuscular applications is intended to be illustrative and not limiting.

In the treatment of treating cardiac arrhythmias, sometimes the result of a neuromuscular disorder, the inventive device can be positioned within, on, through, or adjacent to heart tissue in order to affect or block electrical conductions that cause symptoms such as atrial fibrillation, pacing defects, hypotension and hypertension. The inventive devices and methods can replace the current practice of RF ablation, surgical procedures (such as the Maze procedure) and anti-arrhythmia drugs.

Proper shape, geometry, and placement of the devices can result in treating the tissue in a similar shape and fashion as those in the aforementioned treatments. The shape of the treatment of the typical Maze procedure can be replicated with the proper physical shape and placement of the inventive device. One embodiment of a device for a method of treating cardiac arrhythmia is a device similar to a rivet. The first end of the rivet would pass through the desired location of the myocardium and be positioned or seated on the external or internal surface, depending on approach. The second end of the rivet combination would be slid along the shaft of the rivet and seated on the opposite side of the myocardium as the first end of the rivet. The first and second end would then be advance towards each other resulting in compression, elongation or mechanical stressing of the myocardial tissue between and proximate to the rivet. The amount of mechanical stressing would be controlled by the distance form the first end to the second end.

The inventive devices and methods can be used in the treatment of cardiomyopathy. A primary cause of cardiomyopathy is a lack of the proteins dystrophin and collagen, the same protein deficiency that exists in the skeletal muscles and leads to generalized weakness, wasting and respiratory complications. Dystrophin and collagen is also needed by cardiac muscle, and its lack can lead to the loss of cardiac muscle cells under the stress of constant contraction. It is know that mechanical forces on tissues can generate increased deposition of collagen fibers within muscular tissues and strengthen these tissues. In the treatment of cardiomyopathy, the inventive devices can provide methods of selectively, broadly or focally, generating mechanical stresses that result in the therapeutic deposition or increased formation of collagen fibers. These fibers can then strengthen myocardial tissues muscle and retard or reversing the effects of cardiomyopathy. This phenomena can also be used to treat other diseases and illnesses that affect tissue strength and connective tissue orientation, density and volume.

Many neurological disorders are a result of improper conduction of electrical currents in various brain tissues. In the case of Parkinson's disease, the conduction currents in the thalamus tissues become disorganized and cause conditions associated with the disease. Likewise, in epilepsy errant currents cause various levels of seizures. In cases of dystonia, errant currents originate in the basal ganglia. Depression and schizophrenia are associated with various electrochemical defects in other portions of the brain. Also, pain symptoms such as trigeminal neuralgia are associated with multiple sclerosis. Paralysis is normally a condition that results from brain injury, nerve damage, or nerve severing.

The localized stresses generated by the inventive device called a Mechanical Stress Device (MSD), will control, inhibit and direct current conduction by reorienting and/or reorganizing the electrical bias of the neurological tissues. In addition, applications for the MSD include compression of selected nerves in order to control, mediate, or suppress conduction along the nerve fibers and bundles that are associated with certain neurologic disorders. The localized stresses also can affect activate or suppress baroreceptors within arteries, veins, heart tissue and other tissues and organs. Affecting the baroreceptors can allow control of various physiologic functions such as sinus rhythm, sympathetic nervous system, blood pressure, hormonal activity and metabolism as examples. The inventive devices and methods can affect the wall of the carotid sinus, a structure at the bifurcation of the common carotid arteries. This tissue contains stretch receptors that are sensitive to mechanical and electrical forces. These receptors send signals via the carotid sinus nerve to the brain, which in turn regulates the cardiovascular system to maintain normal blood pressure. The proper method of use and placement of the inventive device can manipulate the baroreceptors and achieve regulation of the cardiovascular system in order to control blood pressure levels. For example, when place proximate to the carotid sinus, the MSD will apply localized stresses that modify or modulate the stretch baroreceptors. The MSD can be complemented with electrical properties and features that can provide additional affects to the baroreceptors function.

The MSD can be placed internal or external to arteries and veins in order to achieve desired activation of baroreceptors. MSD can be attached to external body plane; skin.

The MSD can also be utilized as an electrically conductive device that creates an electrical connection or "bridge" between targeted anatomical tissues. This technique may facilitate tissue-to-tissue communication, aid in regenerating nerve connections, or affect the electrical conduction between the SA and AV nodes of the heart to overcome pacing defects. Likewise, an MSD may be placed proximate to the pulmonary vein in order to quell, block or mitigate abhorrent conduction currents that cause atrial fibrillation.

In the case of Parkinson's disease, an MSD is implanted in the tissues proximate to the thalamus and induce localized stresses that cause depolarization of the thalamus tissue and thus eliminate or reduce the symptoms of the disease. In Dystonia, the MSD is positioned proximately to the basal ganglia and disrupts the electrical disturbances associated with this disorder.

The same effect is utilized in the treatment of epilepsy and other tissues when the MSD is installed in the targeted brain tissues. An MSD may be place on or adjacent to the vagus nerve in order to mechanically and or electrically cause stimulation. This stimulation of the vagus nerve can provide therapeutic treatment of epilepsy and depression. In addition, MSD stimulation of the vagal nerve can provide treatment for heart function such as cardiac ventricular output, rhythm, and systemic blood pressure. The devices and methods associated with the MSD can also be utilized in the sinuses and various ventricles of the brain to treat personality disorders such as schizophrenia or depression. Additionally, migraine headaches and Tourette's Syndrome may be treated with the MSD technology. In general, the methods of the invention guide the placement of the device to ensure a therapeutic effect from the device.

In another application, Vestibular disorders, which may interact with blood pressure and heart rate control, can be treated and controlled. The vestibular system is one source of information about uprightness and the system has an affect on the cardiovascular system. Proper placement and manipulation of the vestibular nerve with one or more of the MSD design embodiments can alleviate or control heart rate and blood pressure, as well as physical balance.

The MSD technology may also be used to affect the neurologic reponse of the digestive system in order to control appetite, digestion or metabolism. In addition, using the previously invented methods and devices in this and the cross referenced patent and applications by Mische, the MSD technology can be used to treat urge or stress incontinence by affecting nerve conduction and neuromuscular function. Also, the neurological and neuromuscular function of the reproductive system can be treated and controlled by using the MSD technology to modify transport and expression of hormones, sperm, ovum, and fluids.

The MSD can be permanently implanted or used acutely and then removed. Likewise, the device can be fabricated of biodegradable materials that are placed chronically and allowed to biodegrade over time.

The devices and methods can be used alone of in conjunction with other therapies.

Examples of electrical therapy with various MSD embodiments are given and they include pacing, depolarization, ablation, and tissue alteration.

BRIEF DESCRIPTION OF THE DRAWINGS

Throughout the several views of the drawings several illustrative embodiments of the invention are disclosed. It should be understood that various modifications of the embodiments might be made without departing from the scope of the invention.

Throughout the views identical reference numerals depict equivalent structure wherein.

DETAILED DESCRIPTION

The device and methods, which are similar to those discussed in the patent application filed on Nov. 19, 1999 by Mische entitled, "Mechanical Devices for the Treatment of Arrhythmias" which is incorporated by reference herein.

Throughout the description the term mechanical stress device MSD refers to a device that alters the electrical properties or chemical properties of physiologic tissues. The device may be made of metal such as Nitinol or Elgiloy and it may form an electrode for electrical stimulation. One or more electrodes may be associated with it. The MSD may incorporate fiber optics for therapeutic and diagnostic purposes. The device may also be made from a plastic or other non-metallic material. The MSD may also incorporate a covering of polymer or other materials. The MSD may also be a composition of different materials. The MSD may be smooth or have cutting or abrasive surfaces. The MSD may have, but not limited to, other elements that protrude from the contour of the surfaces such as spindles, splines, ribs, points, hooks, wires, needles, strings, and rivets.

The MSD may be implanted for chronic use or for acute use. Biodegradable materials that degrade or dissolve over time may be used to form the MSD. Various coatings may be applied to the MSD including, but not limited to, thrombo-resistant materials, electrically conductive, non-conductive, thermo-luminescent, heparin, radioactive, or biocompatible coatings. Drugs, chemicals, and biologics such as morphine, dopamine, aspirin, lithium, Prozac, genetic materials, and growth factors can be applied to the MSD in order to facilitate treatment. Other types of additives can be applied as required for specific treatments.

Electrically conductive MSDs, or MSDs with electrode elements, may be used with companion pulse generators to deliver stimulation energy to the tissues. This electrical therapy may be used alone or in combination with other therapies to treat the various disorders. Electrical therapies may be supplied from implantable devices or they may be coupled directly to external generators. Coupling between the MSD and external generators can be achieved using technologies such as inductive, capacitive or microwave coupling as examples. The MSD may also be designed of geometries or materials that emit or absorb radioactive energies.

Figure 1:
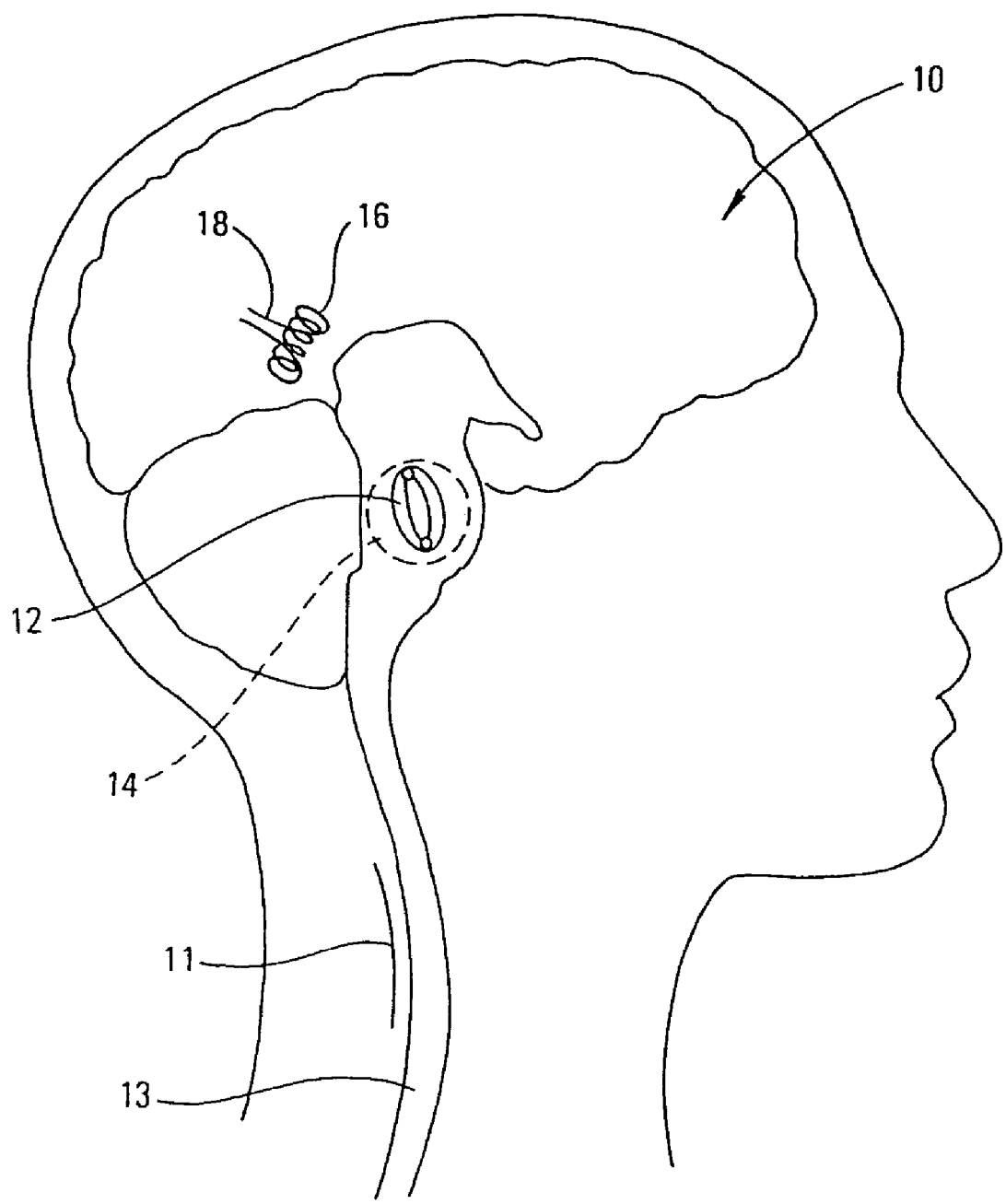
FIG. 1. is a schematic diagram of the head showing mechanical stress devices implanted within brain tissue.

FIG. 1 is a schematic diagram showing several possible locations and geometries for the mechanical stress device (MSD) within the brain 10. A multi-element splined MSD 12 is positioned proximate to the thalamus 14. In this case, the treatment is for Parkinson's Disease. A coil MSD 16 is positioned proximate to the trigeminal nerve 18 for treatment of trigeminal neuralgia. A wire form MSD 11 is positioned adjacent to the spinal cord 13.

Figure 2:
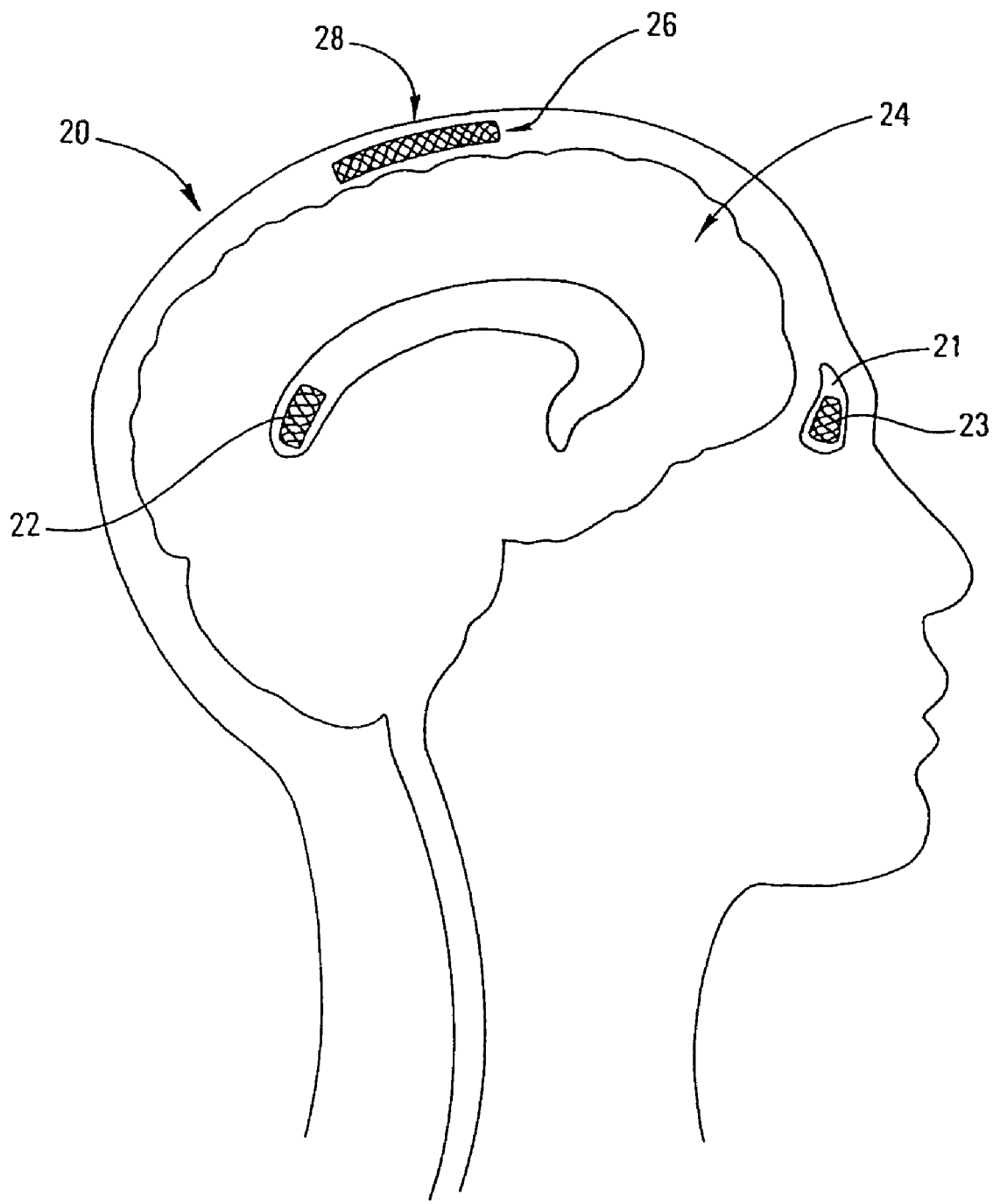
FIG. 2. is a schematic diagram of the head showing mechanical stress devices implanted in the frontal sinus, lateral ventricle of brain, and between the skull and brain tissue.

FIG. 2. is a schematic diagram of the head showing various locations of MSDs of a tubular mesh form. An MSD 22 is located in the lateral ventricle of the brain 24. Another MSD 26 is positioned between the skull 28 and the brain 24. Within the frontal sinus 21 an MSD 23 is positioned.

Figure 3:
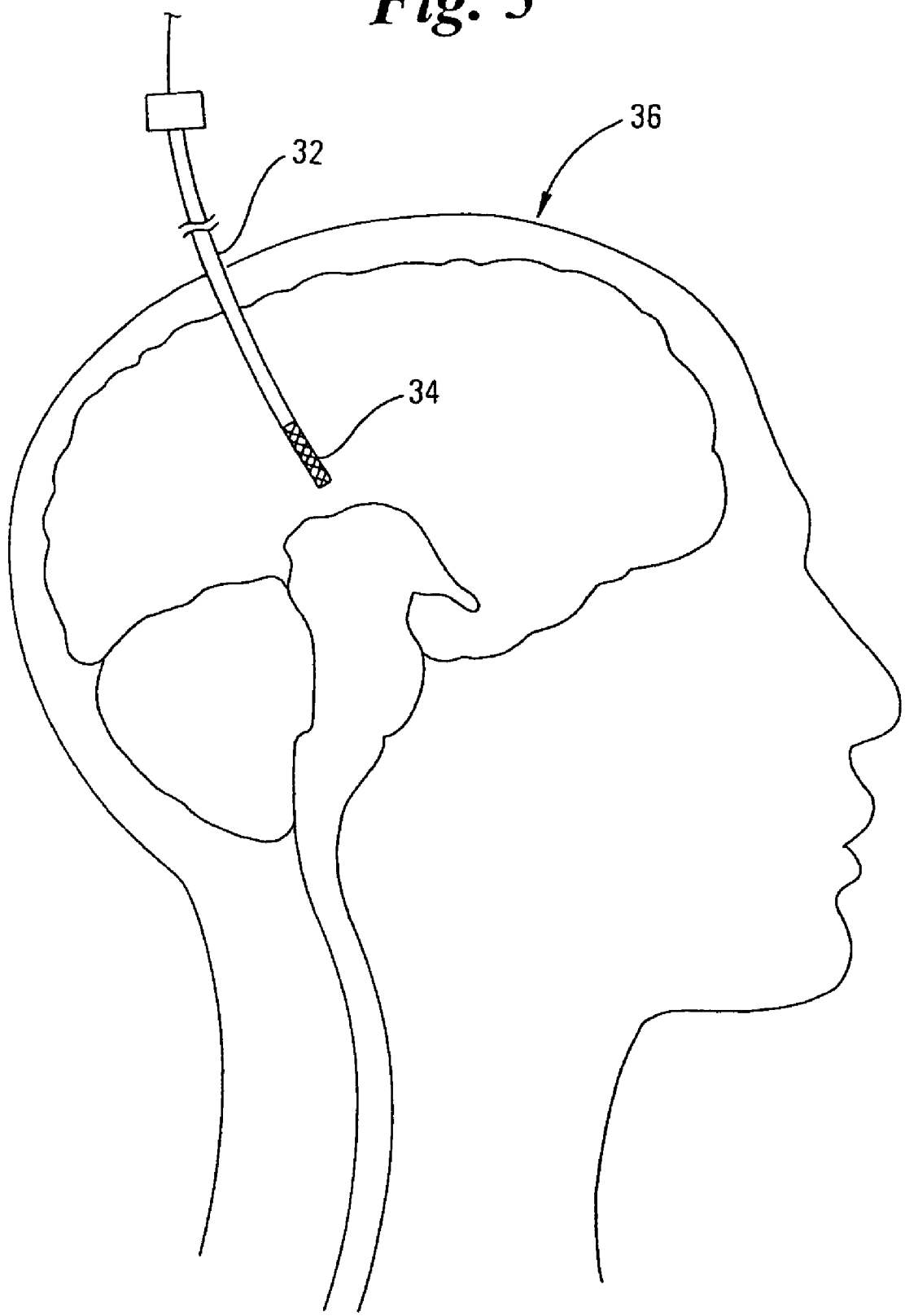
FIG. 3. is a schematic diagram of the head showing the mechanical stress device delivery system.
Figure 4:
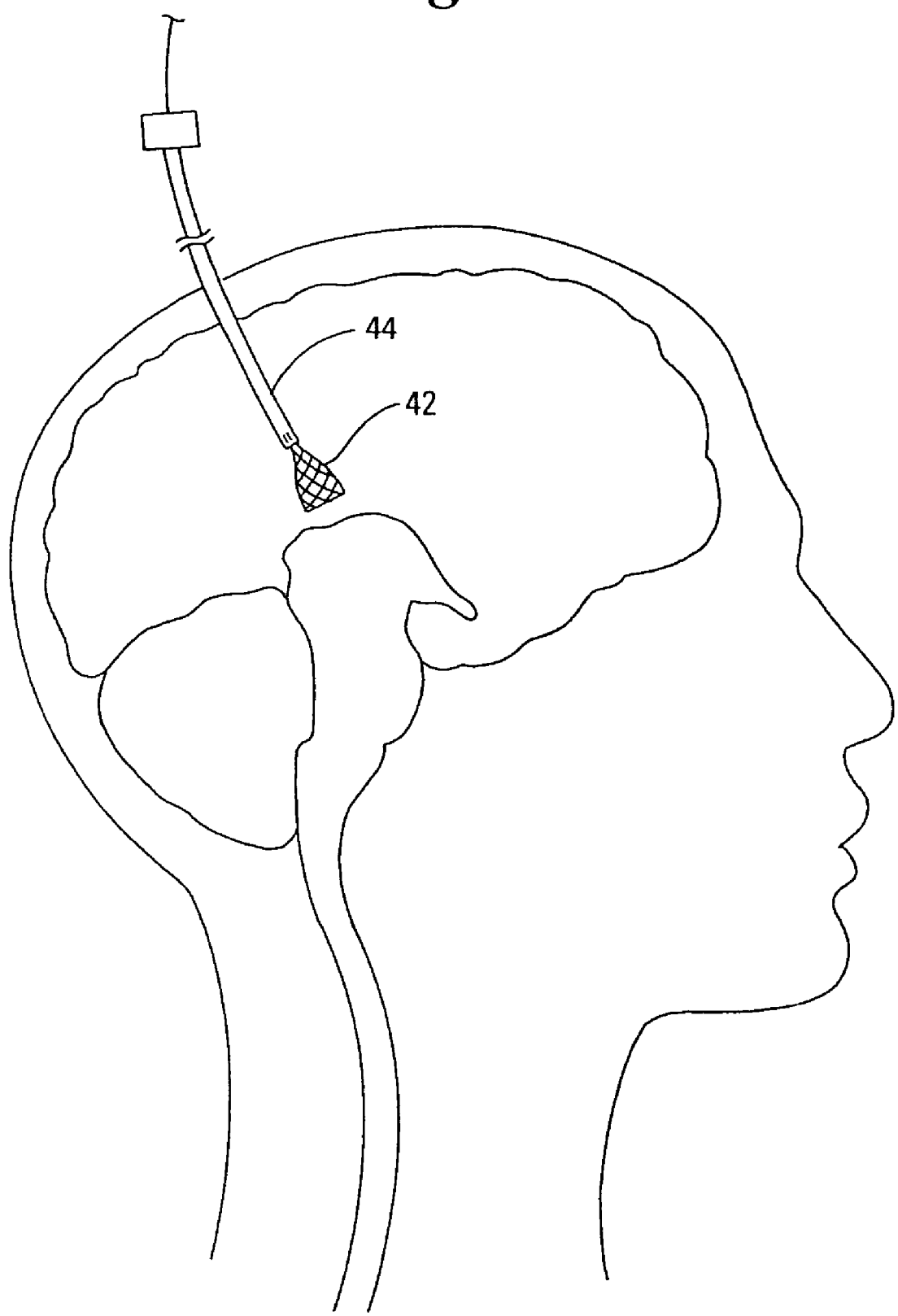
FIG. 4. is a schematic diagram of the head showing the mechanical stress device delivery system.

FIG. 3 and FIG. 4 should be considered together. Together the two figure show the deployment of an MSD.

FIG. 3 is a schematic diagram of a tubular mesh type MSD delivery system. The tubular catheter 32 delivers the tubular mesh MSD 34. The first stage of implantation is navigation of the device to the selected site through the skull 36.

FIG. 4 shows the tubular mesh 42 expanding into position as it emerges from the lumen of the delivery catheter 44. In the self-expanding case, the tubular mesh has a predetermined maximum expandable diameter. The mesh can be made of a shape-memory material such as Nitinol so that when subjected to body temperature the structure expands. With shape memory materials, the shape of the expanded device can be predetermined. Additionally, the device can be retrieved, repositioned, or removed by using its shape memory characteristics. In general the MSD may be used acutely or chronically depending on the disease state of the patient.

Figure 5:
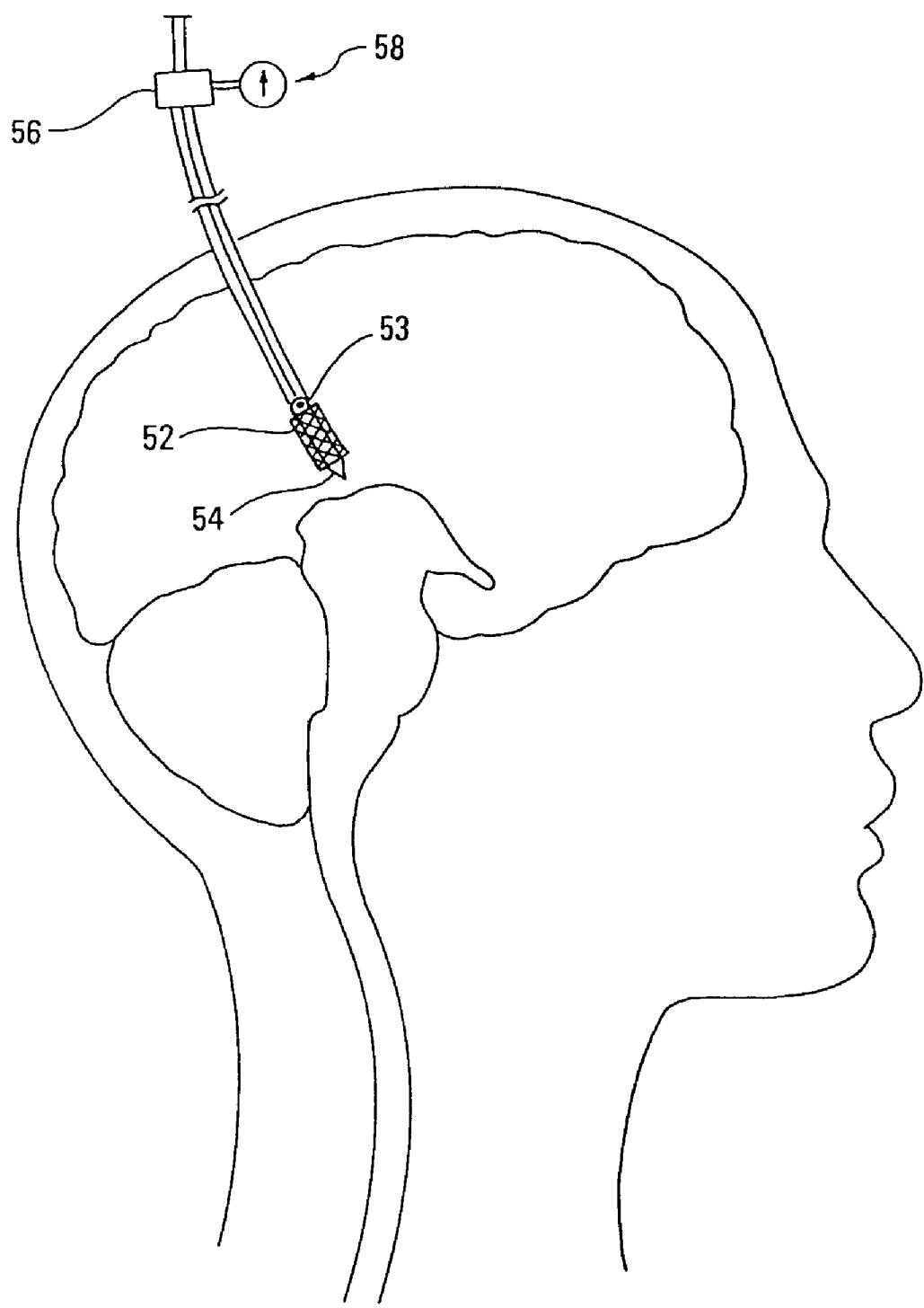
FIG. 5. is a schematic diagram of the head showing the mechanical stress device delivery system.

FIG. 5 shows an alternate balloon expanded MSD 52. In this alternate embodiment a balloon 54 may be used to expand the device within or proximate to selected tissues. In the balloon expandable case, the balloon may have a predetermined minimum or maximum diameter. In addition, the balloon shape can be made to provide proper placement and conformance of the device based on anatomical requirements and location. The balloon may be covered with electrically conductive material. The balloon may be inflated via a syringe 56 and a pressure gauge 58. For example an electrode site 53 may be connected to a remote pulse generator (not shown) to stimulate or ablate the site. The stimulator may activate the electrode either chronically or acutely.

Figure 6:
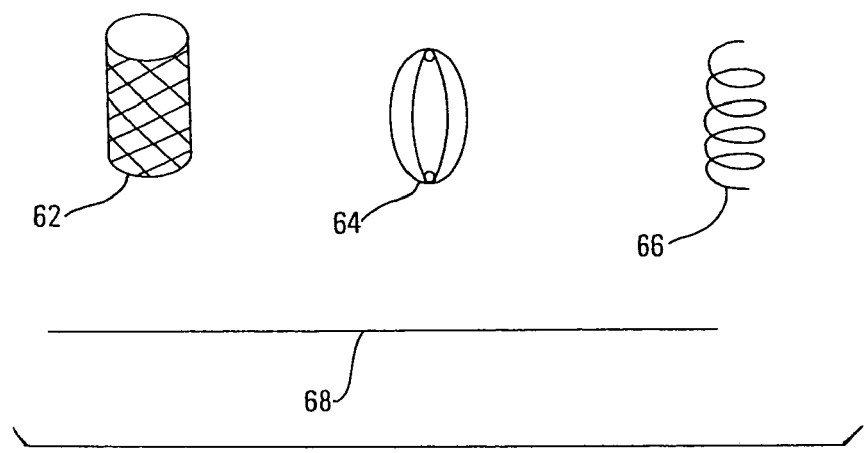
FIG. 6. shows a variety of MSD designs.

FIG. 6 shows a variety of possible MSD shapes and geometries. A tubular mesh 62, a multi-element spline 64, a coil 66, a wire 68 are all acceptable shapes for the MSD although each shape may be specifically adapted to a particular disease state. Other anticipated geometries include clam shells, spherical shapes, conical shapes, screws, and rivets. Although the preferred embodiments consider expandable geometries, alternate geometries can be constructed that retract, compress, collapse, crimp, contract, pinch, squeeze or elongate biologic and physiologic tissues as long as they provide one or more of the desired mechanical, electrical or chemical effects on the selected tissue. Delivery methods for the different possible geometries are anticipated, too.

Figure 7:
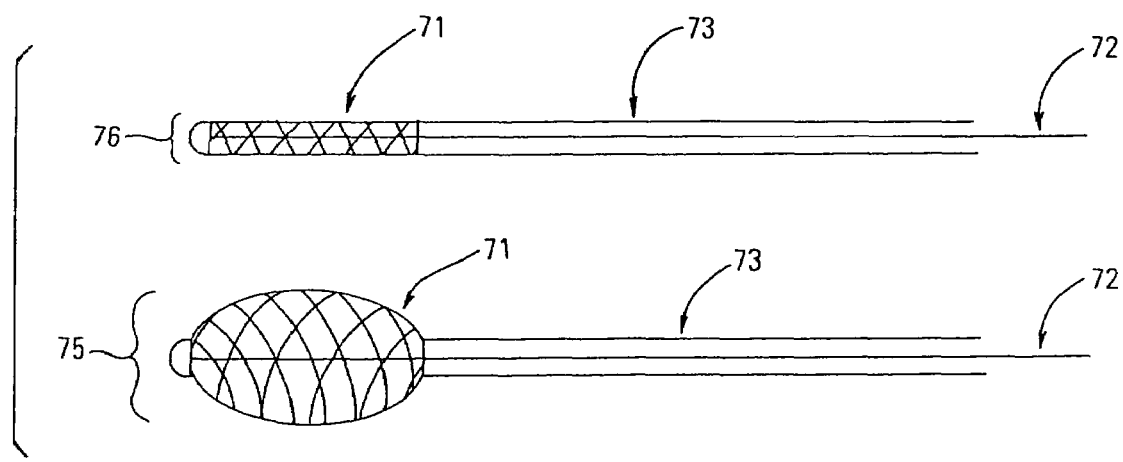
FIG. 7. depicts an MSD, which is manually expanded contracted.

FIG. 7 shows two states of a manually expandable MSD device 71. The device consists of a coaxial shaft 72 and tube 73 arrangement. Attached to the distal end of the shaft 72 and the tube 73 is a braided mesh tube MSD 71. When the shaft 72 and tube 73 are moved opposite of the other by manipulating the proximal ends, the MSD 71 expands 75 or contracts 76. In this case, the MSD 71 can be made of any structure that expands and contracts such as a coil, splined-elements, etc. The various methods of expanding and contracting these structures are, but not limited to, push-pull, rotation, and balloon manipulation. In this type of device, direct connection to either an electrical generator, laser, or monitoring system can be made. In addition, it be envisioned that a device of similar nature be connected to a mechanical energy source, such as rotational or vibrational, in order to increase localized stresses.

The MSD can also utilize devices such as a balloon catheter, expanding devices, or wedges that impart stress or certain levels of localized trauma to selected tissues. The resultant stress and trauma affect the tissues so that current conduction in modified. It is envisioned that any of these devices can be used alone or in conjunction with other treatment modalities in order to provide the desired therapeutic result.

In general, the MSD will have a relaxed or minimum energy state. However the device or the implantation procedure should stretch or stress the device so that it applies a persistent force to the tissues to alter conduction in the strained tissues. In this sense the implanted MSD is not in a fully relaxed state after implantation. In some instances the MSD will cause the tissues to yield or tear generating altered conduction.

Preferably, the MSD is delivered in a minimally invasive procedure such via a catheter or other device. X-ray imaging, fluoroscopy, MRI, CAT scan or other visualization means can be incorporated into the procedural method. In general the devices maybe introduced with cannulas, catheters or over guidewires through naturally occurring body lumens or surgically prepared entry sites. It should be apparent that other surgical and non-surgical techniques can be used to place the devices in the target tissue.

It should be apparent that various modifications might be made to the devices and methods by one of ordinary skill in the art, without departing from the scope or spirit of the invention.

In another embodiment, MSD's may also be designed in order to optimize coupling with external sources of electromagnetic energies via inductive or capacitive coupling. These energies can be utilized to electrically activate the MSD in order to impart voltages and currents to tissues to augment the mechanoelectric and or mechanochemical effects of the MSD. The MSD can be designed in such a fashion where it acts similarly to an implanted antenna. Likewise, the MSD may function primarily as an antenna with little, if any, mechanoelectric effects. The coupled electrical energy to this MSD antenna can be directly imparted to the tissues adjacent to the implanted. The received energy may be used to charge a circuit that is integrated into the MSD structure that discharges at a certain level directing electrical energy to the desired or adjacent tissue. For example, the circuit may consist of resistors, capacitors, inductors, amplifiers, diodes or other components that assist in producing the desired function and effects. The circuit may consist of separate nodes for input and output voltages or it may have one node for both input and output.

In another embodiment, the MSD may consist of circuitry that can automatically treat the neurological defects by utilizing the electrical energy generated by the physiologic tissues in which the MSD is implanted. In the case of epilepsy, focal tissues generate errant currents that result in seizure activity. These affected focal tissues are readily identified with standard CAT or MRI imaging systems and an MSD can then be implanted into these tissues. When the errant currents are generated, these currents charge the circuitry in the MSD. When the circuitry is charged to a predetermined level, it discharges back into the affected focal tissues and resolves the errant currents. A RC time constant circuit can be utilized for this MSD version. Amplifiers, signal generators and other processing circuitry can be incorporated into an MSD in order to increase or modify the output.

In another embodiment, the MSD has a covering to increase the surface area of the device. The covering can encompass the entire device or selected portions and can be positioned on the outside or inside surface. Such a covering can be made of polymers such as Teflon, polyethylene, polyurethane, nylon, biodegradable materials or other polymeric materials. The covering can also be made of a fine metal or polymeric mesh. In all cases, the covering can be bonded to the surface of the MSD or applied as a loose sheath-type covering. The covering can have therapeutic materials applied or incorporated into the covering material itself. Examples of the therapeutic materials include drugs, stem cells, heparin, biologic materials, biodegradable compounds, collagen, electrolytes, radiopaque compounds, radioactive compounds, radiation-activated substances, or other materials that enhance the clinical effects and/or procedures.

In another embodiment, the MSD may have a material that substantially fills its interior space. Such a material would prevent formation of spaces or voids once an expandable MSD is placed. The materials may be fibrous, gels, porous, foam or sponge-like and may be incorporated with polymers, glass, metals, radioactive compounds, biologic tissues, drugs, or other suitable materials that may enhance clinical effective and/or procedures. The materials would be flexible enough to allow expansion of the MSD and can be made of polymers, glass, metal, biologic tissues, drugs, or other suitable materials. Although not limited to, examples of biologic materials include stem cells, brain cells and matter, thalamic tissues, and collagen.

The use of appropriate materials may also provide certain electrical properties to the MSD that enable it to receive, store and/or transmit electrical energy. The dielectric properties of these materials would provide electrical capacitor properties and function to the MSD. This provides the benefit of creating an electrical circuit that can receive, store and discharge energy from various sources. The source may be external generators that couple capacitively, inductively or magnetically, RF energy from a predetermined portion of the electromagnetic spectrum to the MSD. In addition, the source may be an electrical generator connected by a wire or a cable to the MSD.

Another means of generating therapeutic electrical energy is to utilize galvanic effects. Proper material selection and interaction with physiologic fluids and tissues would result in galvanic currents or electrochemical reactions being generated by the MSD. Generally, dissimilar metals or materials would be used in order to optimize the generation of galvanic currents. These currents could provide constant therapeutic electrical energy levels to the desired tissues. This could potentially benefit patients suffering from Parkinson's, epilepsy, pain, depression, migraines, etc. The galvanic currents can also be used to energize, activate, or charge circuits or batteries that provide monitoring, diagnostic or therapeutic effects. This technology could also be used for intravascular devices such as stents in order to prevent thrombosis or hyperplasia or to energize implantable sensors or monitoring devices. Galvanic devices can also be used to treat peripheral pain, generate revascularization of myocardial tissues, treat tumors, provide electrical potential for drug transport into tissues, treat endometriosis, or to power, energize, activate, operate or charge other medical devices such as cardiac pacemakers, defibrillators or other electrical generator based systems.

In another embodiment, the MSD may be a structure that completely or partially slices into tissue. The slicing action cleaves or separates the tissue physically breaking the electrical conduction paths. In this case, the MSD can reach complete or partial state of expansion. In the case of complete expansion, the residual stress to the tissue would be approaching zero, while the partial expansion would result in a combined clinical effect via part mechanical stress and part slicing of tissue.

Additional methods of constructing MSD's include using three-dimensional structures such as wedges, slugs, clips, rivets, balls, screws, and other structures that impart stress to the tissues. Materials such as open-cell polymers, gels, liquids, adhesives, foams can also be inserted or injected into tissue and tissue spaces in order to generate the desired amount of stress. These types of material could also have the additional benefit of being therapeutic agents or carriers for therapeutic agents.

Another MSD structure can consist of a balloon that is positioned at desired location, inflated within the tissue, and then detached and left in an inflated state. Examples of inflation media can be fluids, gels, foams, pharmaceuticals, and curable resins.

Other embodiments of MSD composition include construction using magnet and magnetic materials that complement the localized effects of the MSD by controlling the electrical properties of the tissues using gradients and fields. In the case where the MSD is composed of magnet materials, the magnetic field emanating from the magnetic materials would bias electric fields within the tissues. This effect can control the direction of current conduction within the tissues. In the case where the MSD is composed of magnetic materials that interact with magnetic gradients and fields, an external magnet placed proximate to the head can physically manipulate the MSD. Movement of the magnetic would cause movement of the MSD. The manipulation would result in dynamic stresses to the tissues adjacent to the MSD, thus affecting the electrical properties of the tissues and potentially resolving seizures or tremors.

Other MSD can be built with an integrated circuit consisting of a resistor, capacitor, and an inductor. The inductor couples with the external electromagnetic energy and the resulting current generated in the inductor charges the capacitor. Based on the RC time constant of the circuit, the capacitor charges to a certain level and then discharges directly to the desired tissues and the errant currents are disrupted by this discharge. A combination of electromagnetic coupling and direct connection incorporates a generator with a transmission coil and a ground connection made directly to the patient, providing a closed-loop circuit. The ground connection can be made directly to the skin of the patient using a clip or a grounding pad such as used during electrosurgical procedures. The pad may be applied to the patient with tape, bands or adhesives. The ground connection may also be implanted on or within tissue. External generators may be manually operated by the patient or other person or may be automatically operated utilizing monitoring systems that identify seizures or tremors and energize the MSD. Likewise, automatic circuitry such as the aforementioned RC-timing circuit can be used. The generators may also be programmed to energize at a certain predetermined sequence, rate and level. In the treatment of mania, depression, schizophrenia or similar disorders, the generator may provide a constant output to maintain a consistent state of electrical condition of the tissues. For convenience, the external generators may be attached directly to the head or incorporated into a hat, helmet, or band. Alternately, the transmission coil separately may be attached directly to the head or incorporated into a hat, helmet, scarf or band. The coil may encompass the entire head or specific portions in order to attain desired coupling with the MSD. In addition, strain gauge technology can be incorporated that can measure and correlate the amount of mechanical stress and strain imparted to tissues or stress and strains imparted to the device by tissues and active organs such as vessels, hearts, valves, and other organs and tissues. Such data can be used to provide a feedback means by which to control the MSD in order to provide treatment as necessary based on the physiologic response or activation.

Likewise, as mentioned previously, the electrical energy inherent in physiologic tissue may also be the source that energizes the circuit. Again, it should be noted that various modifications might be made to the devices and methods by one of ordinary skill in the art, without departing from the scope of the invention.

What is claimed is:

1. A method of treating blood pressure disorders comprising the steps of: identifying the carotid sinus; placing a mechanical stress device proximate to the carotid sinus with a placement device; removing said placement device, whereby said mechanical stress device remains proximate to the carotid sinus; whereby said mechanical stress device affects baroreceptors at said carotid sinus; whereby the affected baroreceptors trigger the sympathetic nervous system control of the blood pressure.

2. A method as in claim 1, where the device is located external to a blood vessel.

3. A method as in claim 1, where the device is located internal to a blood vessel.

4. A method as in claim 1, where the device is directly coupled to an electrical generator.

5. A method as in claim 1, where the device is remotely coupled to an electrical generator.

6. A method of treating cardiac rhythm disorders involving an abhorrent electrical conduction path in the myocardial tissues comprising the steps of: identifying target tissue having the electrical conduction defect responsible for the cardiac rhythm disorder; placing a mechanical stress device in said target tissue with a placement device; removing said placement device, whereby said mechanical stress device remains in said tissue; whereby the mechanical stress modifies the abhorrent electrical conduction path in the myocardial tissue.

7. A method as in claim 6, where the device is directly coupled to an electrical generator.

8. A method as in claim 6, where the device is remotely coupled to an electrical generator.

9. A method as in claim 6, where the device has a sensor circuit.

10. A method as in claim 6, where the device stretches the myocardial tissue.

11. A method as in claim 6, where the device compresses the myocardial tissue.

12. A method as in claim 6, where the device is partially embedded within the myocardial tissue.

13. A method as in claim 6, where the device is in contact with both the external and internal surfaces of the myocardial tissue.

14. A method of treating epilepsy comprising the steps of: identifying the vagus nerve; placing a mechanical stress device proximate to the vagal nerve with a placement device; removing said placement device, whereby said mechanical stress device remains proximate to the vagal nerve; whereby said mechanical stress device affects the conduction of the vagal nerve; whereby the affected nerve the mitigates an epileptic seizure.

15. A method as in claim 14, where the device is directly coupled to an electrical generator.

16. A method as in claim 14, where the device has a sensor circuit.

17. A method as in claim 14, where the device stretches the vagal nerve.

18. A method as in claim 14, where the device compresses the vagal nerve.

* * * * *